(12) United States Patent
Inafuku et al.

(10) Patent No.: US 7,815,951 B2
(45) Date of Patent: Oct. 19, 2010

(54) METHOD FOR PRODUCING BLASTING FERMENTATION-TREATED BAGASSE

(75) Inventors: Naoshi Inafuku, Okinawa (JP); Tetsuya Fujino, Okinawa (JP); Yutaka Kashiwagi, Tsukuba (JP); Seiji Ohara, Tsukuba (JP); Seiyu Inafuku, Okinawa (JP)

(73) Assignees: Ryukyu Bio-Resource Development Co., Ltd. (JP); Forestry and Forest Products Research Institute (JP); Japan Science and Technology Agency (JP)

( * ) Notice: Subject to any disclaimer, the term of this patent is extended or adjusted under 35 U.S.C. 154(b) by 87 days.

(21) Appl. No.: 11/914,502

(22) PCT Filed: Mar. 20, 2006

(86) PCT No.: PCT/JP2006/305583

§ 371 (c)(1),
(2), (4) Date: Dec. 10, 2007

(87) PCT Pub. No.: WO2006/123474

PCT Pub. Date: Nov. 23, 2006

(65) Prior Publication Data

US 2008/0248161 A1    Oct. 9, 2008

(30) Foreign Application Priority Data

May 16, 2005  (JP) .............................. 2005-143327

(51) Int. Cl.
*A23L 1/308*  (2006.01)
(52) U.S. Cl. ........................................ 426/52; 426/615
(58) Field of Classification Search ................... 426/52, 426/615, 37, 31, 49, 58, 46; 424/242, 254.3; 435/242, 254.3
See application file for complete search history.

(56) References Cited

U.S. PATENT DOCUMENTS 3,751,261 A * 8/1973 Tatara ......................... 426/52
4,028,470 A * 6/1977 Hayashi et al. ............... 426/11
5,501,860 A * 3/1996 Maeda et al. ............... 424/464
5,520,933 A * 5/1996 Yoshida et al. ................ 426/7

FOREIGN PATENT DOCUMENTS

| JP |   53113067 A | * | 10/1978 |
| JP |  2002-204674 |   | 7/2002  |
| JP | 2002204674 A | * | 7/2002  |
| JP |  2004-236634 |   | 8/2004  |
| JP | 2004236634 A | * | 8/2004  |

OTHER PUBLICATIONS

Inafuku et al., Method for Producing Blasting Fermentation-Treated Bagasse, Jul. 2002, JP 2002204674 A, Machine Translation.*
Tatara et al., JP 53113067 (Oct. 1978), Derwent Abstract.*
Inafuku et al., Method for Producing Blasting Fermentation-Treated Bagasse, Jul. 2002, JP 2002204674 A, Machine Translation (from JPO Website).*
Tamaki et al., JP 2004236634 (Aug. 2004), Machine Translation (from JPO Website).*
Ishihara et al., Enzymatic degradation of cellulose in variously pre-treated bagasse, 1983 (no month), 193-200.*
Kusumoto, *Aspergillus oryzae* with and without a homolog of aflatoxin biosynthetic gene ver-1, 1998 (no month), Appl Microbiol Biotechnol, 50:98-104.*

* cited by examiner

*Primary Examiner*—Rena L Dye
*Assistant Examiner*—Saeeda Latham
(74) *Attorney, Agent, or Firm*—Kenneth H. Sonnenfeld; King & Spalding LLP (57) ABSTRACT

The invention is related to a method for producing a steamed, exploded, and fermented dietary fiber, comprising the steps of: subjecting a hemicellulose-containing plant resource to a steam treatment followed by an explosion treatment (2.5 Mpa, 70 seconds); mixing wheat bran into this steamed and exploded material; adjusting water content of this mixture to about 50%; subsequently preparing koji with the use of a koji fungus; adding water to the koji thus obtained; mixing the steamed and exploded material into a koji dispersion wherein koji is dispersed into water; adjusting water content of this mixture to about 50%; subsequently fermenting the mixture. This method produces a useful material as a food material and a health supplement, by a simple process, with efficiency, and at a low cost.

9 Claims, 5 Drawing Sheets

Fig. 1

Antioxidative activity of obtained hot water extract of food material (1 mg/ml)

Antioxidative activity of obtained fraction of food material

Fig. 5

Polyphenol amount in fungus-fermented or enzymatically-treated bagasse

METHOD FOR PRODUCING BLASTING FERMENTATION-TREATED BAGASSE

TECHNICAL FIELD

The present invention relates to a processed dietary fiber wherein a fermentation treatment is performed to a steam-exploded material, which contains a xylo-oligosaccharide, an antioxidant active substance and a dietary fiber, being obtained from a hemicellulose-containing plant resource such as bagasse, and to a method for producing the same. More particularly, the present invention relates to processed dietary fiber wherein a fermentation treatment is performed to a steam-exploded material which contains a xylo-oligosaccharide, an antioxidant active substance and a dietary fiber, being obtained by preparing koji from a hemicellulose-containing plant resource such as bagasse which has been steamed and exploded, and fermenting the hemicellulose-containing plant resource such as bagasse with the use of this koji; and to a method for producing the same.

BACKGROUND ART

It is known that dietary fibers have useful physiological effects when they are taken orally. For example, it is known that they have effects such as a laxative effect, normalization of cholesterol metabolism, improvement of sugar tolerance, promotion of insulin secretion, and elimination of toxic substances from the body.

On the other hand, it is also known that xylo-oligosaccharides and substances having an antioxidative activity have useful physiological effects Xylo-oligosaccharides reach the intestines without being digested by digestive enzymes of human, and have effects such as improvement of constipation symptoms and improvement of enteric environment, and have a characteristic that they exhibit a great effect on the improvement of enteric environment even at low doses. Further, it has been revealed that substances having an antioxidative activity express preferable effects such as antihypertension, elimination of active oxygen, suppression of peroxide production, suppression of rise in cholesterol, and promotion of fat metabolism.

Accordingly, food, etc., by which these effects can be safely obtained and which can be produced at low cost are demanded, and it is also demanded that food materials to be used as raw materials of such foods are provided at low prices. By applying the food materials to foods, it becomes possible to easily produce foods, etc., having these effects. In order to obtain these food materials at low prices, efficient production is desired.

Conventionally, the following method has been known as a method for producing food materials thus described: a method comprising the steps of conducting a fermentation treatment wherein a koji fungus is inoculated into and grown in a dietary fiber as a raw material derived from husks of cereals and beans, and then conducting a hydrolysis treatment by acids (for example, Patent Document 1). In addition, the following method has been known as a method for producing a dietary fiber which contains a xylo-oligosaccharide and which has an antioxidant activity: a method for producing an antioxidant dietary fiber comprising the steps of subjecting a plant fiber such as bagasse to a high pressure steam treatment and an explosion treatment, and then converting the treated fiber into sugar by an enzymatic treatment using xylanase and cellulase (for example, Patent Document 2).

Other than the methods mentioned above, the following method has been known as a method for producing a xylo-oligosaccharide having an effect on controlling intestinal functions, etc.; a method for obtaining a xylo-oligosaccharide comprising the steps of subjecting a chemical pulp as a raw material to an enzymatic treatment and hydrolyzing the treated pulp (for example, Patent Document 3). Further, the following methods have been disclosed: a method for obtaining a cereal grain distilled liquor containing a large amount of ferulic acid, which is an antioxidant substance, by using a koji fungus (for example, Patent Document 4), and a method for separating and obtaining ferulic acid, which is a substance having an antioxtdative activity, from a byproduct of liquors produced with the use of a koji fungus which produces citric acid (for example, Patent Document 5).

Patent Document 1: Japanese Laid-open Patent Application No. 06-7099
Patent Document 2: Japanese Laid-open Patent Application No. 2002-204674
Patent Document 3: Japanese Laid-open Patent Application No. 2003-48901
Patent Document 4: Japanese Laid-open Patent Application No 2004-236634
Patent Document 5: Japanese Laid-open Patent Application No. 2003-52351

DISCLOSURE OF THE INVENTION

An Object to be Attained by the Invention

However, there were various problems in conventional production methods. Examples of such problems are as follows: in case where a hydrolysis treatment is necessary, time is required for a production process; and in case where hydrolysis by acid is conducted, neutralization is required and thereby the production process becomes complicated, and salts are produced.

Further, in case where an enzyme treatment is necessary, there are problems that, for example, practical use is difficult due to economic reasons. Enzymes are generally expensive, and as adjustment of enzyme solutions, etc., is necessary when enzymes are used, new facilities were required in some cases.

The object of the present invention is to provide, by solving the problems mentioned above, a method for producing a material which contains a xylo-oligosaccharide, an antioxidant active substance and a dietary fiber, and which is useful as a food material or health supplement, by a simple process, with efficiency, and at a low cost.

Means for Attaining the Object

The present inventors have made a keen study for effective use of bagasse, a waste obtained when squeezing sugar cane, and have conducted the following steps: subjecting bagasse to a steam treatment followed by an explosion treatment; mixing a fermentation substrate into this steamed and exploded bagasse; adjusting water content of this mixture to about 50%; and preparing koji with the use of a koji fungus. As a result, it took about 2 weeks for the koji fungus to proliferate and grow in the steamed and exploded bagasse, and in many cases, bacterial contamination occurred and accumulation of xylo-oligosaccharides was not observed. Therefore the present inventors have conducted the following steps: preparing koji with the use of a part of the steamed and exploded bagasse to be used as a raw material; adding water to the koji thus obtained; mixing an about 10-fold amount of the steamed and exploded bagasse into a koji dispersion wherein koji is dispersed in water; adjusting water content of this mixture to about 50%; and subsequently, fermenting the mixture. By conducting these steps, the present inventors have thus found that it is possible to obtain a useful food material which contains xylo-oligosaccharides such as xylobiose and xylotriose, an antioxidant active substance such as ferulic acid, and a dietary fiber. The present invention has been thus completed.

In other words, the present invention relates to: (1) a method for producing a processed dietary fiber comprising the steps of: subjecting a hemicellulose-containing plant resource to a steam treatment followed by an explosion treatment; mixing a fermentation substrate into this steamed and exploded material; adjusting water content of this mixture; subsequently preparing koji with the use of a koji fungus; adding water to the koji thus obtained; mixing the steamed and exploded material into a koji dispersion wherein koji is dispersed into water; adjusting water content of this mixture; and subsequently, fermenting the mixture: (2) the method for producing a processed dietary fiber according to (1) mentioned above, wherein the steam and explosion treatments are conducted under a condition of 2.0 to 3.0 Mpa; (3) the method for producing a processed dietary fiber according to (1) or (2) mentioned above, wherein the hemicellulose-containing plant resource is ground in advance, and subsequently the steam treatment is conducted and followed by an explosion treatment; (4) the method for producing a processed dietary fiber according to any one of (1) to (3) mentioned above, wherein wheat bran is used as a fermentation substrate; (5) the method for producing a processed dietary fiber according to any one of (1) to (4) mentioned above, wherein an equal amount of water is added to a mixture of the steamed and exploded material and the fermentation substrate to adjust its water content; (6) the method for producing a processed dietary fiber according to any one of (1) to (5) mentioned above, wherein a koji fungus having a high xylanase activity obtained by conducting single spore isolation from *Aspergillus sojae* (NFRI1147) is used as koji fungus, (7) the method for producing a processed dietary fiber according to any one of (1) to (6) mentioned above, wherein 5- to 10-fold amount of the steamed and exploded material used for koji preparation is used as steamed and exploded material to be mixed into the koji dispersion; (8) the method for producing a processed dietary fiber according to any one of (1) to (7) mentioned above, wherein the steamed and exploded material is mixed into the koji dispersion and water content of this mixture is adjusted to about 50%; (9) the method for producing a processed dietary fiber according to (8) mentioned above, wherein a calcium-containing compound is further added to adjust pH to 4.0 to 6.9; (10) the method for producing a processed dietary fiber according to any one of (1) to (9) mentioned above, wherein a treatment to terminate the fermentation is conducted after 48 to 72 hours of fermentation; (11) the method for producing a processed dietary fiber according to any one of (1) to (10) mentioned above, wherein the processed dietary fiber is in a form of dried fine powder; and (12) the method for producing a processed dietary fiber according to any one of (1) to (11) mentioned above, wherein the hemicellulose-containing plant resource is bagasse.

The present invention further relates to: (13) a processed dietary fiber which contains 50 wt % or more of dietary fiber obtained by the method for producing according to any one of (1) to (12) mentioned above, (14) a processed dietary fiber which contains 50 wt % or more of dietary fiber and 0.5% or more of xylobiose and xylotriose; (15) a processed dietary fiber which contains 50 wt % or more of a dietary fiber and 1 mg or more of ferulic acid per 100 g; (16) a processed dietary fiber which contains 50 wt %, or more of dietary fiber, 0.5% or more of xylobiose and xylotriose, and 1 mg or more of ferulic acid per 100 g; and (17) a processed dietary fiber according to any one of (14) to (16) mentioned above, which is a fermented and steam-exploded bagasse.

BEST MODE OF CARRYING OUT THE INVENTION

With regard to the method for producing a processed dietary fiber (steam-exploded and fermented) of the present invention, there is no particular limitation as long as it is a method comprising the steps of: subjecting a hemicellulose-containing plant resource to a steam treatment followed by an explosion treatment; mixing a fermentation substrate into this steamed and exploded material; adjusting water content of this mixture; subsequently, preparing koji with the use of a koji fungus; adding water to the koji thus obtained: mixing the steamed and exploded material into a koji dispersion wherein koji is dispersed into water; adjusting water content of this mixture; and subsequently, fermenting the mixture. As the hemicellulose-containing plant resource mentioned above, in addition to bagasse, which is a waste obtained by compressing sugar cane replicated in the process of producing sugars from sugar cane, other plant resources containing insoluble xylan such as rice, corn cores, and woods are exemplified. Hereinafter, the case where bagasse is used as a hemicellulose-containing plant resource will be described as an example.

In case where bagasse is used as a hemicellulose-containing plant resource, the processed dietary fiber of the present invention is called as fermented and steam-exploded bagasse, and the fermented and steam-exploded bagasse is obtained by a method comprising the steps of: subjecting bagasse to a steam treatment followed by an explosion treatment; mixing a fermentation substrate into this steamed and exploded material; adjusting water content of this mixture; subsequently, preparing koji with the use of a koji fungus; adding water to the koji thus obtained; mixing the steamed and exploded material into a koji dispersion wherein koji is dispersed in water adjusting water content of this mixture; and subsequently, fermenting the mixture.

The steam treatment followed by an explosion treatment mentioned above is not particularly limited as long as it is a treatment comprising the steps of: steaming bagasse with high-temperature and high-pressure water vapor in a pressure-resistant reaction container to hydrolyze xylan to a certain degree; and then opening the valve provided on the pressure-resistant reaction container at once to release the vapor instantaneously into atmospheric pressure. By this steam treatment followed by an explosion treatment, bagasse can be ground due to synergistic effects of the chemical reaction caused by the hydrolysis and the physical reaction caused by the adiabatic expansion of water. As conditions of this steam treatment followed by an explosion treatment, the followings are exemplified: at 1.0 Mpa to 3.0 Mpa for 30 seconds to 10 minutes, preferably at 2.0 Mpa to 2.8 Mpa for 1 to 5 minutes, more preferably at 2.4 Mpa to 2.6 Mpa for 60 to 80 seconds. Further it is preferred that bagasse is ground in advance, and subsequently to perform a steam treatment followed by an explosion treatment. With regard to the degree of grinding, it is preferred to grind bagasse coarsely such that its average particle diameter is in a range of 2 to 5 nm, particularly 3 to 4 mm, more particularly 3.5 mm.

The bagasse which has been treated with steaming and explosion, is mixed with a fermentation substrate. The fermentation substrate is not particularly limited as long as it is a fermentation substrate wherein a koji fungus can grow when it is mixed into bagasse. From the viewpoint of availability at a low cost, wheat bran, rice bran, molasses, etc., are exemplified as the fermentation substrate, and wheat bran is preferable among them. For example, in case where wheat bran is used as the fermentation substrate, it is possible to blend 1 to 50 parts by weight, preferably 10 to 50 parts by weight, more preferably 40 to 45 parts by weight of wheat bran into 100 parts by weight of steamed and exploded bagasse. When preparing koji, it is necessary to add water to this mixture to adjust its water content, and water is added such that the water content becomes 40 to 60%, preferably 45 to 55%, more preferably about 50%.

With regard to the koji fungus to be used for the koji preparation, there is no particular limitation and koji fungi used for ordinary koji preparation are exemplified. Specific examples include *Aspergillus oryzae* and *Aspergillus sojae*. As koji fungi to be used, strains having a high xylanase activity are preferable because food materials containing a large amount of xylo-oligosaccharides can be obtained. By this xylanase, xylo-oligosaccharides are produced from hemicellulose. Though methods for preparing mutant strains with the use of UV rays and mutagenic agents can be used as a method for preparing strains having a high xylanase activity, natural mutant strains obtained by conducting single spore isolation are preferable from a safety standpoint. As to the xylanase activity, an activity which liberates 1 μmol of xylose per minute from xylan at 40° C. is defined as 1 unit, and as a method for measuring the xylanase activity, publicly known methods can be used. With regard to the koji fungi having a high xylanase activity, it is preferred that their xylanase activities are 0.35 unit/g or higher in accordance with this condition. In addition, among xylo-oligosaccharides, those mainly containing xylobiose and xylotriose are preferable because they are highly resistant to stomach acid than other oligosaccharides and therefore they reach the intestines without being digested. From the standpoint of the effect on controlling intestinal functions, etc., it is preferred that the ratio of xylo-oligosaccharides mainly consisted of xylobiose and xylotriose, being contained in the steam-exploded and fermented bagasse, is 3.9% or more. Further, in order to prepare the steam-exploded and fermented bagasse which contains 3.9% or more of xylo-oligosaccharides mainly consisted of xylobiose and xylotriose, it is preferred that a koji fungus having a high xylanase activity obtained by conducting single spore isolation from *Aspergillus sojae* (NFRI1147) is used as a koji fungus. It is preferred that koji is prepared by conducting culture at 28 to 32° C., in particular, at 30° C., for 5 to 7 days.

Then, the prepared koji is dispersed in water, the steamed and exploded bagasse mentioned above is mixed into this koji dispersion, water content of this mixture is adjusted, and subsequently the mixture is fermented. As a steamed and exploded material to be mixed into the koji dispersion, 5- to 10-fold amount, preferably 8- to 9-fold amount of the steamed and exploded material used for the koji preparation can be used. It is necessary to adjust the water content by adding water to the mixture wherein the steamed and exploded bagasse is mixed into the koji dispersion, and water is added so that the water content becomes 40 to 60%, preferably 45 to 55%, more preferably about 50%. Preferably, the mixture is fermented by conducting culture at 28 to 32° C., in particular, at 30° C., for 48 to 72 hours. It is preferred that a treatment to terminate the fermentation is conducted after fermentation from the standpoint of preventing over-fermentation. As a treatment to terminate the fermentation, a method which involves exposure to vapor at 80 to 100° C. for 30 minutes is specifically exemplified.

Further, it is preferred that the method of the present invention comprises a step of adding a calcium-containing compound to adjust pH to 4.0 to 6.9. By adding a calcium-containing compound, the drop of pH can be prevented, and by appropriately adjusting the amount of the calcium-containing compound to be added to adjust pH to 4.0 to 6.9, the fermentation efficiency can be improved, and accordingly, fermentation time can be shortened. Examples of calcium-containing compounds of the present invention include calcium chloride, calcium citrate, calcium gluconate, calcium glycerophosphate, acid calcium pyrophosphate, calcium hydroxide, calcium carbonate, calcium lactate, calcium sulfate, monobasic calcium phosphate, dibasic calcium phosphate, tribasic calcium phosphate, calcium pantothenate, calcium dihydrogen pyrophosphate, coral calcium, dolomite, eggshell calcium, bovine bone meal calcium, scallop shell calcium, and milk calcium. Among them, calcium hydroxide, eggshell calcium, bovine bone meal calcium, scallop shell calcium and milk calcium are preferably exemplified.

As the steam-exploded and fermented bagasse obtained by the production method of the present invention, dried products, in particular, dried fine powders are preferred. Favorable example of the average particle diameter of the dried fine powders is 1 mm or smaller, preferably 500 μm or smaller, more preferably 200 to 300 μm. In addition, as steam-exploded and fermented bagasses obtained by the production method of the present invention, the followings are preferred: those containing 3.9% or more of xylo-oligosaccharides mainly consisted of xylobiose and xylotriose; those containing an antioxidant active substance such as ferulic acid and exhibiting an antioxidative activity, and those containing 50 wt % or more of a dietary fiber measured by an enzyme method.

Next, with regard to the steam-exploded and fermented dietary fiber (steam-exploded and fermented bagasse) of the present invention, there is no particular limitation as long as it is any one of the followings: those obtained by the production method of the present invention mentioned above and containing 50 wt % or more of dietary fiber; those containing 50 wt % or more of dietary fiber and 0.5% or more, preferably 1% or more, more preferably 2% or more, still more preferably 3% or more, particularly 3.9% or more of xylobiose and xylotriose; those containing 50 wt % or more of dietary fiber and 1 mg or more of ferulic acid per 100 g; those containing 50 wt % or more of dietary fiber, 0.5% W or more, preferably 1% or more, more preferably 2% or more, still more preferably 3% or more, particularly 3.9% or more of xylobiose and xylotriose, and 1 mg or more of ferulic acid per 100 g. By using these processed dietary fibers (steam-exploded and fermented bagasse) for processed food, it becomes possible to easily provide foods which contain xylo-oligosaccharides, an antioxidant active substance and a dietary fiber. Examples of processed foods include noodles, candies, cookies, cereals, confectioneries (snacks), seasoned powders for sprinkling over rice, processed livestock products, processed fish products, canned food, juice, soft drinks, nutrition-supplement drinks, dog and cat food, and fish food. In addition, the steam-exploded and fermented dietary fibers (steam-exploded and fermented bagasse) can be formulated in forms of tablets, granules, capsules, syrups, etc., by ordinary methods, and can be used as health supplements.

Hereinafter, the present invention will be described more specifically with reference to Examples, however, the technical scope of the present invention is not limited to these exemplifications.

EXAMPLE 1

Selection of Koji Fungus

On a potato dextrose agar (Nissui Pharmaceutical, Co., Ltd.), *Aspergillus sojae* NFRI11147 strain was well grown and allowed to sporulate. After sporulation, its spores were suspended in 0.9% saline containing 0.1% Tween 80, and this spore solution was smeared on a potato dextrose agar (Nissui Pharmaceutical, Co., Ltd.). Static culture was conducted at 25° C. for 2 to 3 days to form independent colonies, and 12 strains showing a high growth rate were separated from about 500 colonies. The separated strains were inoculated on bagasse-wheat bran media (5 g of steam-exploded bagasse, 5 g of wheat bran, 5 mg of oyster shell calcium, and 50 mL of deionized water) and cultured at 25° C. for 3 to 10 days. Subsequently, 0.5 M of acetic acid buffer (pH 5) was added and the cultures were extracted well. The extracted cultures were filtered through filter paper No. 5 (ADVANTEC) to obtain extract solutions. The xylanase activities of the extract solutions were measured and a natural mutant strain with a high xylanase activity level, 1147-9 strain, was selected. Further, the second single spore isolation operation was repeated in a same manner with the use of the 1147-9 strain as a base material, and 12 strains which grew rapidly were obtained in a same manner. These strains were cultured on bagasse-wheat bran media in a same manner and their xylanase activities were measured. With regard to a strain with the highest activity, the activity was increased from 0.254 U/mg protein, a value measured before the single spore isolation, to 0.453 U/mg protein. The obtained strain with the highest activity was designated as 1147-9-6 strain. The NFRI1147 strain is stored in National Food Research Institute, which is an independent administrative institute, and is shared out with third parties under certain conditions.

The xylanase activity mentioned above was measured as follows. To 0.1 ml of a 100 mM phosphate buffer solution (pH 7.0) containing soluble xylan (Sigma) at a concentration of 1%, 0.1 ml of a culture supernatant which had been appropriately diluted with the same butter solution was added, and a reaction was conducted at 37° C. for 10 minutes, and then the reaction was terminated by adding 1.0 ml of a copper reagent. To this mixture, 0.8 ml of the same buffer solution was added such that the total amount becomes 2.0 ml, and then reducing sugars which had been produced were measured with the Somogyi-Nelson method. In other words, the reducing sugars were heated at 100° C. for 15 minutes, and then quickly cooled with running water and subsequently 1.0 ml of Nelson solution was added, and the resultant solution was left still at room temperature for 20 minutes to cause color development. To that solution, 7.0 ml of pure water was added and insoluble substances were removed by centrifugation (3000 rpm, 10 minutes), and then the absorbance at 500 nm was measured. The amount of reducing sugars was calculated on the basis of an analytical curve which had been prepared by measuring xylose in a similar strain. As a blank, a solution to which the copper reagent was added before the addition of the culture supernatant, and wherein color development was caused in a same manner, was used. Further, as to the unit of the enzyme activity, an amount of the enzyme which produces 1 μmol of reducing sugar (as xylose) per minute is defined as 1 unit (U).

(Koji Preparation Process)

A steam explosion treatment was conducted as follows: dried bagasse was coarsely ground with the use of a grinding mill for dried bagasse such that the average particle diameter was becomes 3.5 mm, and the ground bagasse was put into a reaction oven (autoclave); subsequently, heated water vapor was sent into the reaction oven, and a steam treatment was conducted at 2.5 Mpa (220° C.), for 70 seconds; and then, water vapor was quickly discharged from the reaction oven, and the pressure was instantly restored to atmospheric pressure. Into 35 kg of the steamed and exploded bagasse, 15 kg of wheat bran was mixed, and 50 L of water was added to the resultant mixture such that water content becomes about 50 wt %. Then, a koji fungus selected by single spore isolation was inoculated on the mixture, and culture was conducted for 6 days at 30° C. to prepare koji.

(Fermentation Process)

The koji thus prepared was dispersed into 70 L of water, and the resultant dispersion was mixed into 300 kg of steam-exploded bagasse which had been used for koji preparation. Water was added to the resultant mixture such that water content becomes about 50 wt % of the total, and then a fermentation treatment was conducted at 30° C. for 60 hours. Subsequently, a treatment to terminate the fermentation was conducted by exposing the treated mixture to vapor of 80 to 100° C. for 30 minutes. This fermentation-treated substance was dried at a drying temperature of 80 to 100° C. (product temperature) with the use of a disc dryer (Tsukishima Kikai Co., Ltd.), and then a fine grinding treatment was conducted to produce a steam-exploded and fermented bagasse having an average particle diameter of 250 μm. The nutrition composition of this steam-exploded and fermented bagasse is shown in Table 1.

TABLE 1

| General components | g/100 g | Minerals | Mg/100 g |
|---|---|---|---|
| Water | 2.3 | Ca | 833.9 |
| Protein | 2.45 | Mg | 42.8 |
| Lipid | 1.39 | K | 163.6 |
| Carbohydrate | 37.45 | Na | 16.9 |
| Energy | 276.9 | Fe | 45.6 |
| Dietary fiber | 52.41 | Zn | 1.4 |
| Xylo-oligosaccharides (total of xylobiose and xylotriose) | | 3.91% | |

As shown in Table 1, the steam-exploded and fermented bagasse is rich in dietary fibers and contains about 4% of xylobiose and xylotriose. The measurement of xylo-oligosaccharides such as xylobiose and xylotriose was conducted in accordance with the HPLC method with the use of DX-500 (Nippon Dionex K. K.). In addition, the measurement was conducted by a same HPLC method as another method, wherein the column was Biorad Aminex Carbohydrate HPX-42A 300×7.8, at a flow rate of 1.0 ml/min, with water as a mobile phase, and at a column temperature of 80° C.

(Antioxidative Property of Steam-Exploded and Fermented Bagasse)

In order to examine the antioxidative activity of the steam-exploded and fermented bagasse, a DPPH radical scavenging method was conducted. In this test, a hot water-extract solution and an 80% ethanol-extract solution of the steam-exploded and fermented bagasse were used as test samples. The test sample of the hot water-extract solution was prepared as follows: 2 g of the steam-exploded and fermented bagasse was subjected to static extraction with 25 ml of hot water at 80° C. for 20 minutes, and the resultant solution was filtered through filter paper NO. 5 (ADVANTEC); this operation was repeated twice, and the filtrate was filled up to 50 ml to be used as a test sample. Further, the test sample of the 80% ethanol-extract solution was prepared as follows: 1 g of the steam-exploded and fermented bagasse was subjected to static extraction with 10-fold amount of 80% ethanol for 12 hours, and the resultant solution was filtered through filter paper No. 5; this operation was repeated twice, and then the filtrate was evaporated to dryness with a centrifugal evaporator, the resultant substance was adjusted to 1 mg/ml with 80% ethanol to be used as a test sample.

In the DPPH radical scavenging method, a DPPH reagent was dissolved in ethanol, and its concentration was adjusted to 0.1 mM. 1.0 ml of this DPPH solution, 0.95 ml of 0.05 M Tris hydrochloric buffer solution, 1.0 ml of ethanol, and 0.05 ml of test samples were mixed and allowed to react for 30 seconds, and the absorbance at a wavelength of 517 nm was measured with a spectrophotometer (Shimadzu Corporation). As a control, water was used instead of the hot water-extract solution. Further, a hot water-extract solution and an 80% ethanol-extract solution of untreated bagasse were used for comparison. Still further, 1.0 mg/ml of an ascorbic acid solution, 1.0 mg/ml of 80% ethanol solution of α-tocopherol were used as positive controls. The absorbance ratio, when the absorbance of the control was set at 100, was calculated, and the absorbance ratio was used as a residual ratio of DPPH, and it was judged that the smaller the value is the stronger the antioxidative activity is. The results are shown in FIG. 1 and FIG. 2.

Figure 1:
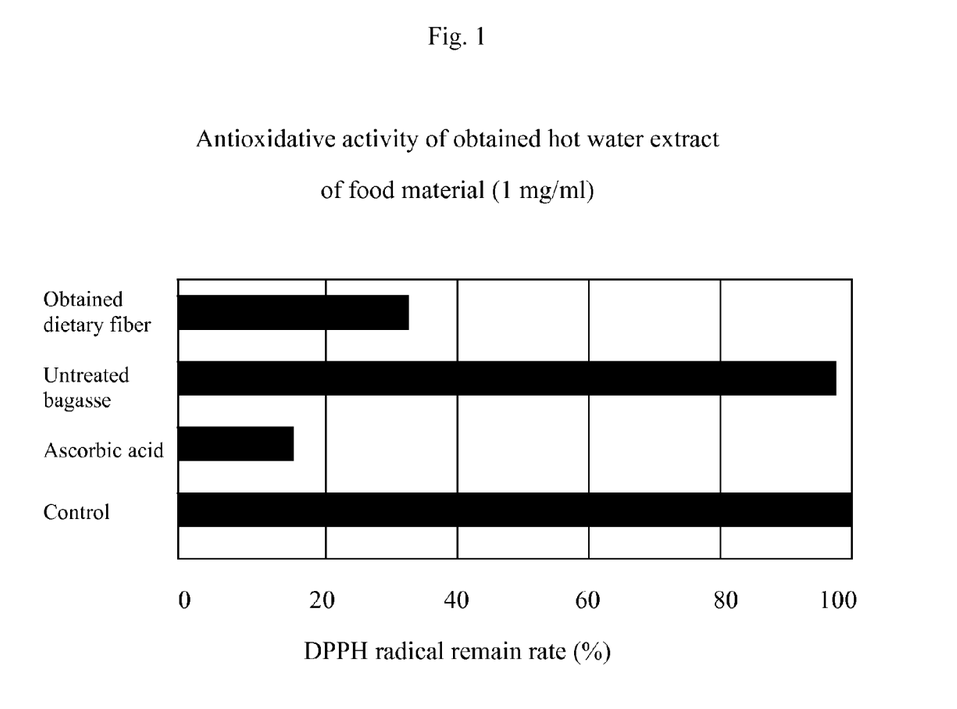
FIG. 1 This is a graph showing the measurement results (n=3) of antioxidative activity measured by the DPPH method, of hot water extracts of the steam-exploded and fermented bagasse obtained by the present invention.
Figure 2:
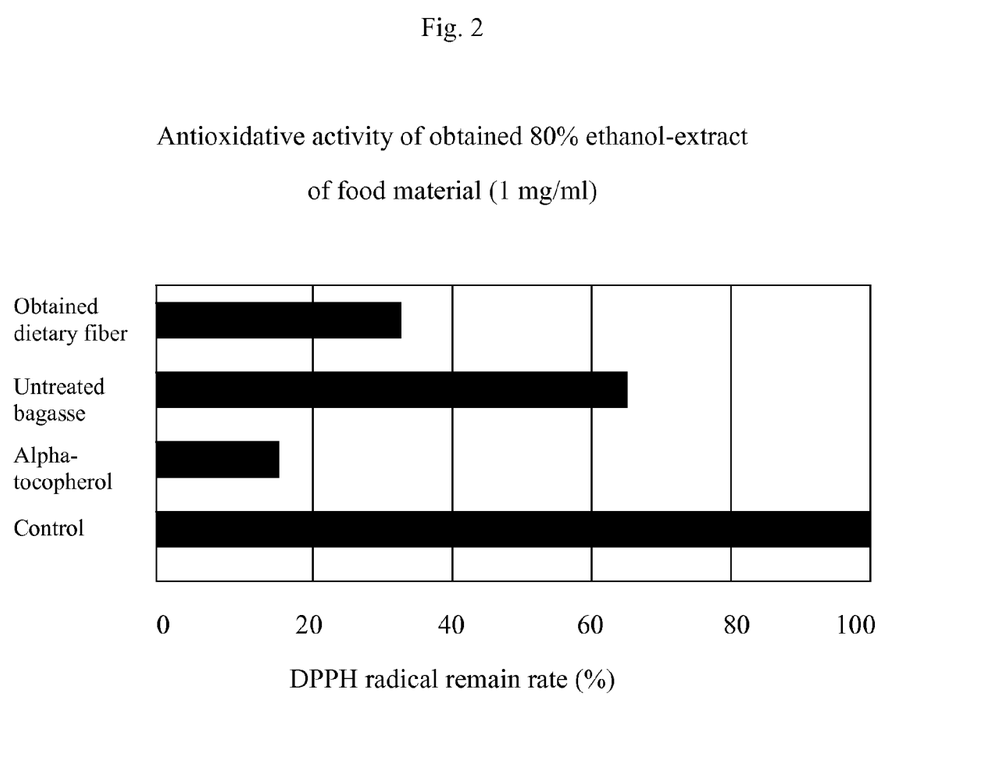
FIG. 2 This is a graph showing the measurement results (n=3) of antioxidative activity measured by the DPPH method, of 80% ethanol extracts of the steam-exploded and fermented bagasse obtained by the present invention.

As shown in FIG. 1 and FIG. 2, it is revealed that both hot water-soluble components and 80% ethanol-soluble components of the steam-exploded and fermented bagasse exhibit an antioxidative activity, and that the antioxidative activity of the untreated bagasse is low. Based on these results, it is revealed that the anti-oxidative activity is remarkably enhanced by the fermentation treatment of the present invention.

(Purification of Substances Having an Antioxidative Activity)

Figure 3:
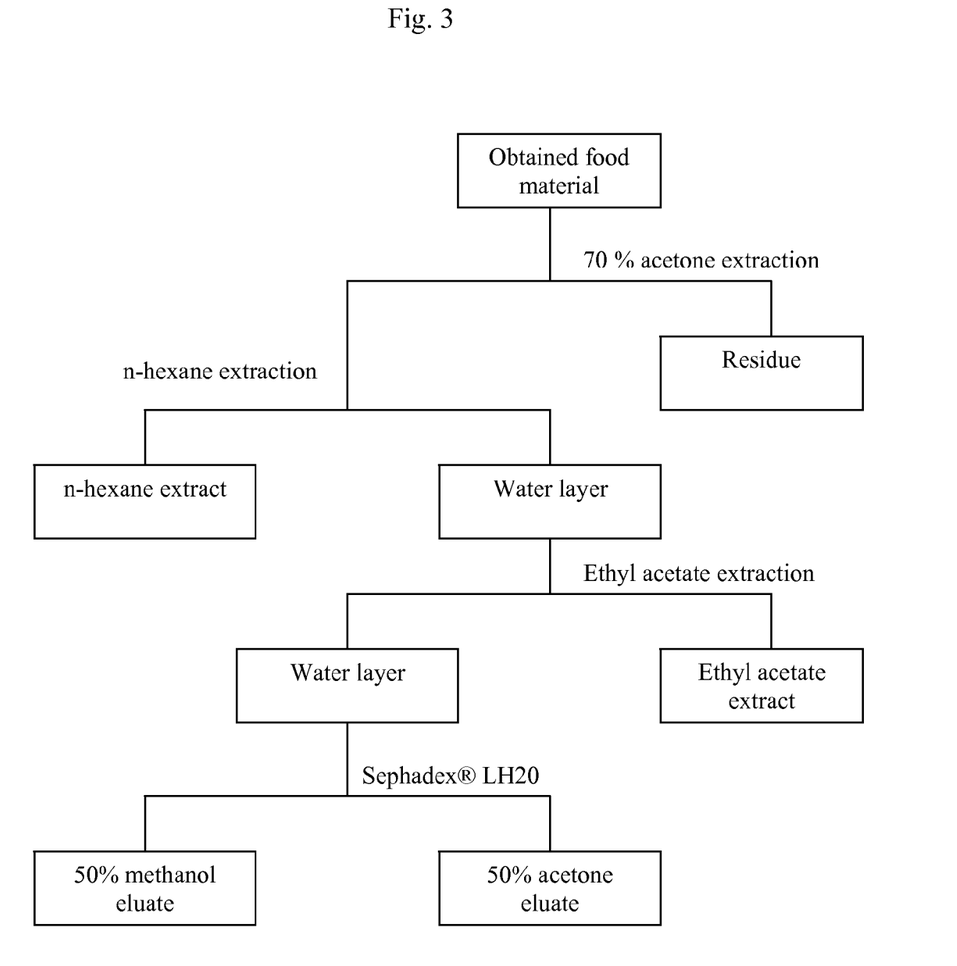
FIG. 3 This is a scheme showing the method for fractionating the steam-exploded and fermented bagasse obtained by the present invention.
Figure 4:
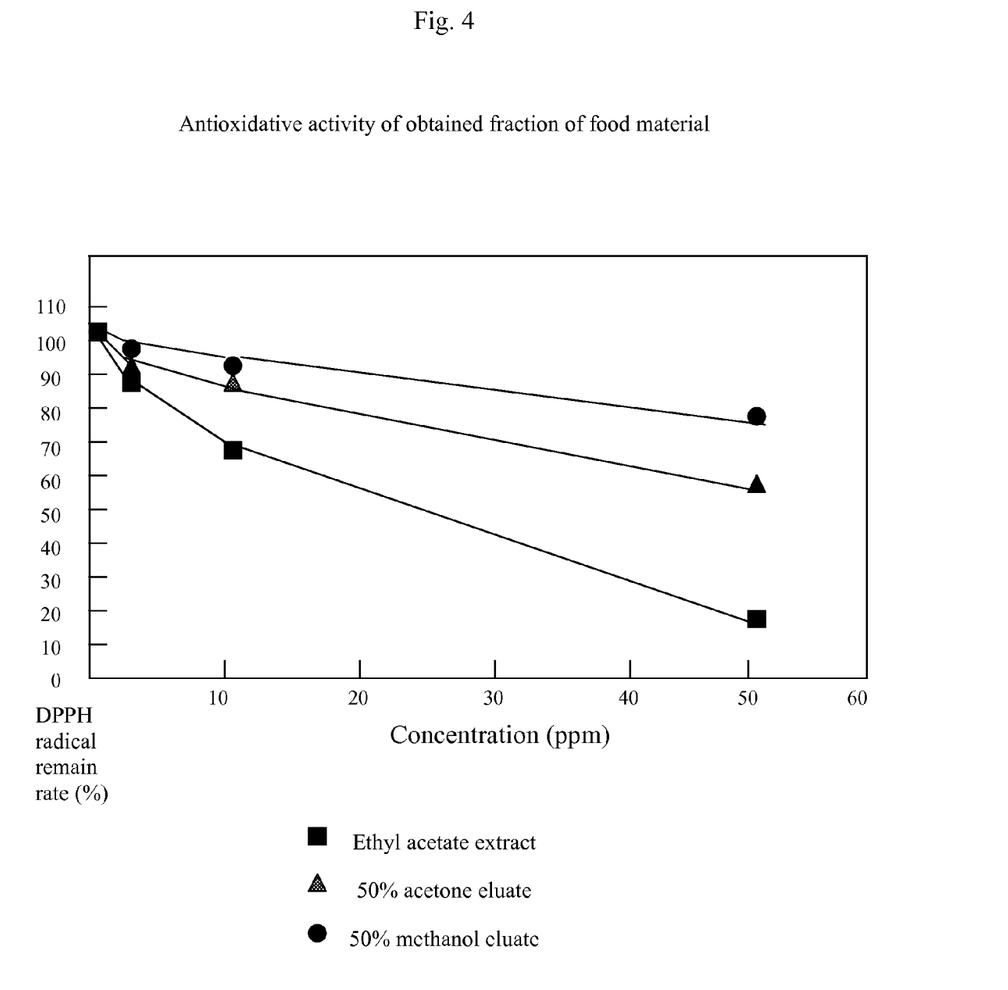
FIG. 4 This is a graph showing the anti-oxidative activity of major fractions when the steam-exploded and fermented bagasse obtained by the present invention is fractionated by the method for fractionating as described in FIG. 3.

The obtained steam-exploded and fermented bagasse was subjected to extraction with a 70% acetone solution, and then extraction with n-hexane and water was conducted in a separatory flask. To the water layer, additional extraction was conducted with ethyl acetate and water. An antioxidative activity was observed in the obtained ethyl acetate, extract. The procedure of fractionation is shown in FIG. 3. In addition, antioxidative activities of major fractions are shown in FIG. 4. For the measurement of the antioxidative activity, the aforementioned DPPH radical scavenging method was used.

(Contents of Para-Hydroxybenzoic Acid and Ferulic Acid)

Figure 5:
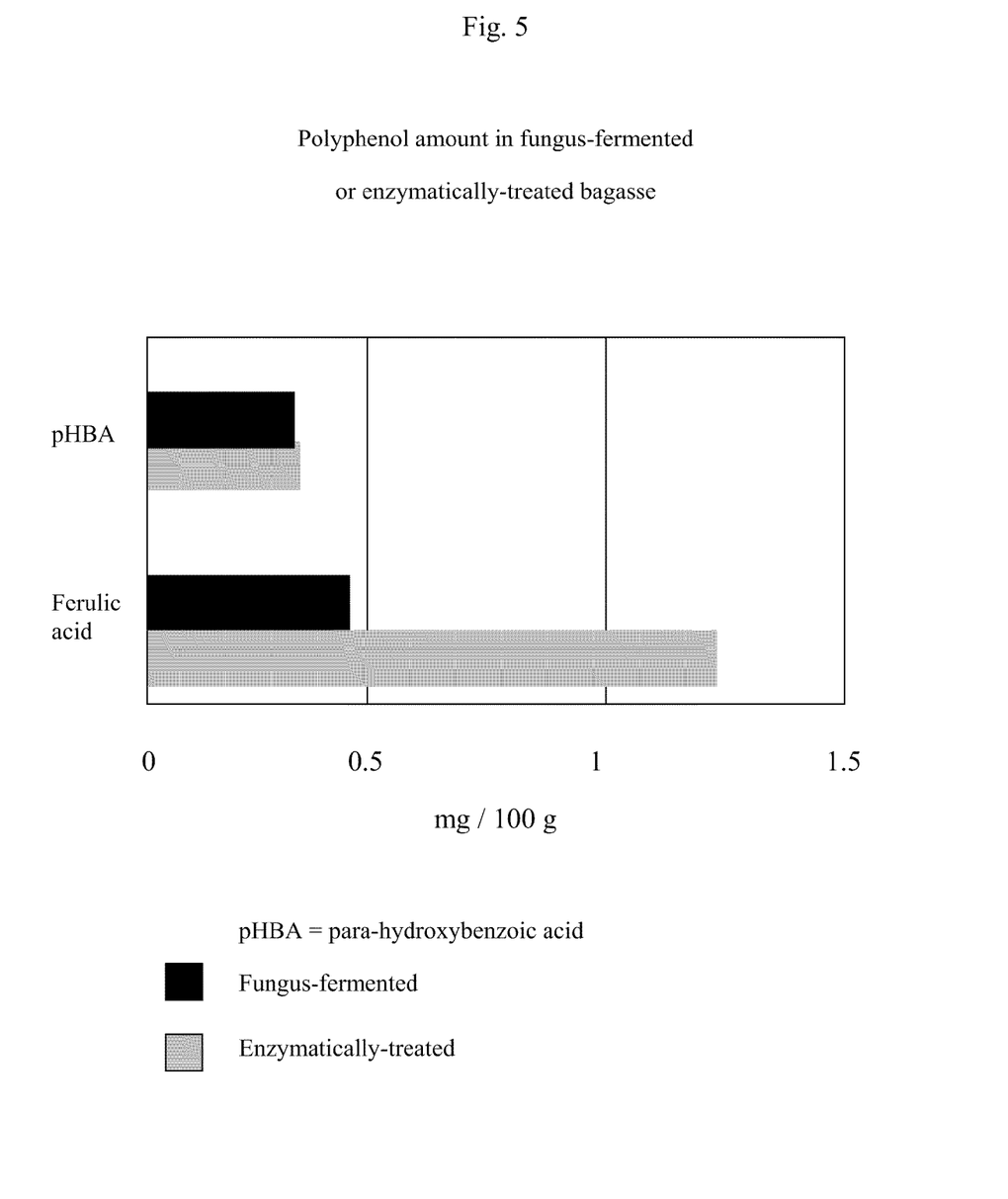
FIG. 5 This is a graph showing the measurement results of the contents of para-hydroxybenzoic acid (pHBA) and ferulic acid in the steam-exploded and fermented bagasse obtained by the present invention and in a steam-exploded and enzymatically-treated bagasse as a control.

The contents of para-hydroxybenzoic acid (pHBA) and ferulic acid in the steam-exploded and fermented bagasse and in the steam-exploded and enzymatically-treated bagasse according to Patent Document 2 as a control, were examined. 1 g of a ground sample was precisely weighed, and 25 ml of 80% methanol was added to the sample to conduct grinding and extraction. Subsequently, centrifugation was conducted at 800 rpm for 15 minutes to obtain a supernatant. This process was repeated twice, and the resultant was filled up to 50 ml and filtered through a filter of 0.45 μm. Then, the filtrate was analyzed by conducting HPLC (ODS column (Nomura Chemical Co., Ltd.) detection wave length 280 nm). As shown in FIG. 5, there is no difference in the contents of para-hydroxybenzoic acid (pHBA) between the steam-exploded and fermented bagasse of the present invention and the steam-exploded and enzymatically-treated bagasse as a control, however, as to the contents of ferulic acid, the steam-exploded and fermented bagasse of the present invention contained 1.25 mg of ferulic acid per 100 mg, which is about 3-fold amount of that contained in the steam-exploded and enzymatically-treated bagasse as a control.

INDUSTRIAL APPLICABILITY

With the method for producing steam-exploded and fermented bagasse of the present invention, it becomes possible to obtain a useful food material which contains xylo-oligosaccharides, an antioxidant substance and a dietary fiber, by a simple process with efficiency, and at a low cost.

The invention claimed is:

1. A method for producing a processed dietary fiber comprising the steps of: subjecting a bagasse to a steam treatment followed by an explosion treatment; mixing a fermentation substrate into the steamed and exploded bagasse; adjusting water content of this mixture; subsequently, preparing koji by inoculating the mixture with the use of a koji fungus having a high xylanase activity obtained by conducting single spore isolation from *Aspergillus sojae* (NFRI1147); dispersing the koji thus obtained into water; mixing steamed and exploded bagasse wherein the amount is 5- to 10-fold of the amount of steamed and exploded bagasse in the prepared koji; adjusting water content of this mixture; and subsequently, fermenting the mixture.

2. The method for producing a processed dietary fiber according to claim 1, wherein the steam and explosion treatments are conducted under a condition of 2.0 to 3.0 Mpa.

3. The method for producing a processed dietary fiber according to claim 1 or 2, wherein the bagasse is ground in advance, and subsequently the steam treatment is conducted and followed by an explosion treatment.

4. The method for producing a processed dietary fiber according to claim 1 or 2, wherein wheat bran is used as a fermentation substrate.

5. The method for producing a processed dietary fiber according to claim 1 or 2, wherein an equal amount of water is added to a mixture of the steamed and exploded material and the fermentation substrate to adjust its water content.

6. The method for producing a processed dietary fiber according to claim 1 or 2, wherein the steamed and exploded bagasse is mixed into the koji dispersion and water content of this mixture is adjusted to about 50%.

7. The method for producing a processed dietary fiber according to claim 6, wherein a calcium-containing compound is further added to adjust pH to 4.0 to 6.9.

8. The method for producing a processed dietary fiber according to claim 1 or 2, wherein a treatment to terminate the fermentation is conducted after 48 to 72 hours of fermentation.

9. The method for producing a processed dietary fiber according to claim 1 or 2, wherein the processed dietary fiber is in a form of dried fine powder.

* * * * *